United States Patent [19]
Orr et al.

[11] Patent Number: 6,050,978
[45] Date of Patent: *Apr. 18, 2000

[54] NEEDLELESS VALVE CONNECTOR

[75] Inventors: Douglas P. Orr, Sandy, Utah; Joseph R. Paradis, Hilton Head Island, S.C.

[73] Assignee: Becton Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/853,286

[22] Filed: May 9, 1997

[51] Int. Cl.⁷ .................................................. A61M 5/00
[52] U.S. Cl. ........................ 604/249; 604/256; 604/905; 251/149.1
[58] Field of Search .................................. 604/246, 247, 604/249, 256, 283, 533; 251/149.1

[56] References Cited

U.S. PATENT DOCUMENTS

| | | | |
|---|---|---|---|
| 3,352,531 | 11/1967 | Kilmarx | 251/149.6 |
| 4,334,551 | 6/1982 | Pfister | 137/614.03 |
| 4,645,494 | 2/1987 | Lee et al. | 604/175 |
| 4,998,927 | 3/1991 | Vaillancourt | 604/283 |
| 5,064,416 | 11/1991 | Newgard et al. | 604/167 |
| 5,122,123 | 6/1992 | Vaillancourt | 604/192 |
| 5,203,775 | 4/1993 | Frank et al. | 604/256 |
| 5,269,771 | 12/1993 | Thomas et al. | 604/213 |
| 5,273,533 | 12/1993 | Bonaldo | 604/83 |
| 5,306,243 | 4/1994 | Bonaldo | 604/86 |
| 5,380,306 | 1/1995 | Brinon | 604/244 |
| 5,402,982 | 4/1995 | Atkinson et al. | 251/149.1 |
| 5,441,487 | 8/1995 | Vedder | 604/167 |
| 5,470,319 | 11/1995 | Mayer | 604/167 |
| 5,474,536 | 12/1995 | Bonaldo | 604/86 |
| 5,474,544 | 12/1995 | Lynn | 604/283 |
| 5,487,728 | 1/1996 | Vaillancourt | 604/86 |
| 5,492,147 | 2/1996 | Challender et al. | 137/614.05 |
| 5,509,433 | 4/1996 | Paradis | 137/1 |
| 5,509,912 | 4/1996 | Vaillancourt et al. | 604/283 |
| 5,514,116 | 5/1996 | Vaillancourt et al. | 604/283 |
| 5,520,666 | 5/1996 | Choudhury et al. | 604/283 |
| 5,549,566 | 8/1996 | Elias et al. | 604/167 |
| 5,549,577 | 8/1996 | Siegel et al. | 604/256 |
| 5,616,129 | 4/1997 | Mayer | 604/167 |
| 5,616,130 | 4/1997 | Mayer | 604/167 |
| 5,616,300 | 4/1997 | Ford et al. | 422/103 |
| 5,700,248 | 12/1997 | Lopez | 604/249 |
| 5,806,831 | 9/1998 | Paradis | 251/149.1 |

FOREIGN PATENT DOCUMENTS

| | | |
|---|---|---|
| WO 93/11828 | 6/1993 | WIPO . |
| WO 96/00107 | 1/1996 | WIPO . |

*Primary Examiner*—Wynn Wood Coggins
*Assistant Examiner*—Deborah Blyvers
*Attorney, Agent, or Firm*—Eric M. Lee

[57] ABSTRACT

A needleless valve connector is disclosed. The needleless valve connector includes a movable diaphragm assembly and an internal central cannula. The proximal portion of the internal cannula has a tapered configuration or is slotted to allow it to be radially compressed to form a tapered configuration. The diaphragm is slit and includes cams formed therein to engage the slotted portion of the internal cannula during downward movement of the diaphragm. The engagement of the cams and the proximal portion of the internal cannula facilitates movement of the diaphragm past the proximal portion of the internal cannula.

9 Claims, 13 Drawing Sheets

NEEDLELESS VALVE CONNECTOR

BACKGROUND OF THE INVENTION

This invention relates to the field of medical devices. More specifically, this invention relates to the field of needleless valve connectors that may be used with medical devices such as catheters, especially intravascular (IV) catheters, IV administration sets, syringes and medicine vials.

In the treatment of patients, valve connectors are needed to facilitate the transfer of fluids between various containers and IV lines or through IV catheters into the patient. For example, where an IV catheter has been placed into a patient to gain access to the patient's vasculature, it may be necessary to infuse medicament through the IV catheter into the patient or to withdraw blood from the patient for blood gas or other analysis. Previously, a rubber or silicone septum was located over the proximal opening in the catheter adapter which prevents blood from flowing out of the catheter but allows the clinician to insert the sharp needle from a standard hypodermic syringe therethrough to infuse fluid from the syringe through the catheter and into the patient or to withdraw fluid into the syringe from the patient. The septum reseals when the needle is withdrawn to thereby prevent back flow of fluid.

In recent years, concern has grown about the risks of infection from diseases such as hepatitis and AIDS (Acquired Immuno-Deficiency Syndrome) that can be spread by the exchange of body fluids via contaminated needles. As a result, much effort has been expended in developing various valve connectors that avoid the use of sharp needles.

One approach has been the development of a needleless valve connector that can be accessed by the blunt male luer tip of a medical device such as a typical syringe. Such a needleless valve connector includes a longitudinally movable diaphragm that controls the flow of fluid through an internal cannula fixed in the needleless valve connector. This internal cannula defines the fluid flow path through the needleless valve connector. The movable diaphragm cooperates with a biasing member such as a spring or other flexible member that biases the top of the movable diaphragm toward the inlet or proximal opening to the needleless valve connector. The opening is typically in the form of a female luer adapter. When the movable diaphragm is adjacent to the inlet of the needleless valve connector, the movable diaphragm occludes the opening to the internal cannula effectively closing the needleless valve connector to fluid flow. When the clinician inserts the male luer tip of the syringe into the female luer adapter of the needleless valve connector, the movable diaphragm is pushed down therein so the internal cannula extends through a pre-formed slit in the movable diaphragm providing a fluid flow path through the needleless valve connector.

It is desirable for the top of the movable diaphragm to be generally flush with the opening to the needleless valve connector so the clinician can swab the top of the movable diaphragm with a disinfectant. This reduces the risk that infection-causing organisms will be infused into the patient when the male luer tip of a medical device contacts the top of the movable diaphragm to move the diaphragm down to open the needleless valve connector and fluid is infused from the syringe through the needleless valve connector.

Although such needleless valve connectors generally perform in accordance with their intended purposes, they could be improved. For example, when the tip of the internal cannula engages the movable diaphragm, the internal cannula has a tendency to core the movable diaphragm. This may cause pieces of the movable diaphragm to be broken off and potentially infused into a patient. In addition, this coring of the movable diaphragm promotes fluid leakage of the needieless valve connector. Finally, the force needed to move the movable diaphragm past the tip of the internal cannula can be quite high making it difficult to operate.

SUMMARY OF THE INVENTION

It is therefore an object of this invention to provide a valve connector that can be accessed without the use of a needle.

It is another object of this invention to provide a needleless valve connector that eliminates coring of the movable diaphragm.

It is still another object of this invention to eliminate fluid leakage through the movable diaphragm of the needleless valve connector.

It is yet another object of this invention to provide a needleless valve connector that is easy to operate.

The needleless valve connector of this invention includes three main parts; a housing, an internal cannula and a movable diaphragm. For ease of manufacture the housing is formed from two pieces with one piece including an integral internal cannula. Of course the internal cannula could be formed separately from the housing and bonded to the appropriate position in the housing. The movable diaphragm uses a biasing mechanism, which is located about the internal cannula in the annular space between the cannula and the housing wall, to bias the movable diaphragm to one end of the housing. The movable diaphragm may be integral with the biasing mechanism.

When the needleless valve connector of this invention is assembled, the housing defines a proximal end and a distal end. The proximal end of the housing defines a proximal opening in the form of a female luer portion. The distal end of the housing defines a distal opening in the form of a male luer portion.

The internal cannula is hollow to define a fluid flow path therethrough and includes a proximal end and a distal end. The proximal end of the cannula is disposed adjacent to the female luer portion of the housing and the distal end of the cannula is in fluid flow communication with the male luer portion of the housing. With this arrangement, fluid can flow in either direction through the internal cannula between the proximal opening in the housing, and the distal opening in the housing when the movable diaphragm does not occlude the proximal opening to the cannula. The proximal portion of the internal cannula has a configuration that facilitates movement of the internal cannula through the movable diaphragm. The proximal portion of the internal cannula can be tapered or slotted. Preferably, it is slotted. Where the proximal portion of the internal cannula is slotted, the proximal portion of the cannula collapses to present a tapered portion when a force is applied to the proximal portion of the cannula in a direction perpendicular to the longitudinal axis of the cannula.

The movable diaphragm fits snugly in the female luer portion of the housing and is formed with a slit extending therethrough. This snug fit provides an external diametrical force around the circumference of the movable diaphragm to urge the slit shut and eliminate fluid leakage therethrough. The distal end of the movable diaphragm includes one or more inclined ramps extending from the surface thereof. These ramps extend away from the slit toward a plane distal to the plane defining the distal end of the slit and perpendicular to the longitudinal axis of the housing.

A biasing mechanism cooperates with the movable diaphragm to bias the movable diaphragm toward the female luer portion of the housing. The biasing mechanism is located about the cannula in the annular space between the cannula and the housing wall. The biasing mechanism may be formed separately from or integrally with the movable diaphragm. The distal end of the biasing mechanism cooperates with a floor formed in the housing located adjacent to the distal end of the housing to allow the biasing mechanism to bias the movable diaphragm in a proximal direction.

When the male luer end of a medical device, such as a syringe, is inserted into the proximal female luer portion of the housing, the male luer end engages the movable diaphragm and forces it toward the distal end of the housing against the bias of the biasing mechanism. As the movable diaphragm is moved distally, the ramps engage the proximal portion of the cannula. Where the proximal end is tapered, the engagement of the cannula and the ramps facilitate opening of the slit in the movable diaphragm. Where the proximal end of the cannula is slotted, the ramps urge the flexible portions of the proximal portion of the cannula together to provide a tapered surface. This minimizes the diameter at the proximal portion of the cannula and thereby facilitates movement of the proximal portion of the cannula through the slit in the movable diaphragm. In addition, the ramps facilitate opening of the slit as a result of the contact by the proximal end of the cannula. Continued distal movement of the male luer end of the medical device into the female luer portion of the housing results in continued distal movement of the movable diaphragm. The cannula thus penetrates through the slit of the movable diaphragm so the proximal end of the cannula is proximal of the proximal end of the movable diaphragm. At this point, the slotted portion of the cannula no longer engages the movable diaphragm. The proximal portion of the cannula can then return to its normal unbiased diameter. In addition, the proximal end of the cannula is in communication with the interior bore of the inserted male luer end of a medical device and fluid can flow through the needleless valve connector. When the male luer end of the medical device is removed the biasing mechanism forces the movable diaphragm proximally so that it returns to a position proximal of the proximal opening to the cannula. In this manner the needleless valve connector is closed to fluid flow.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
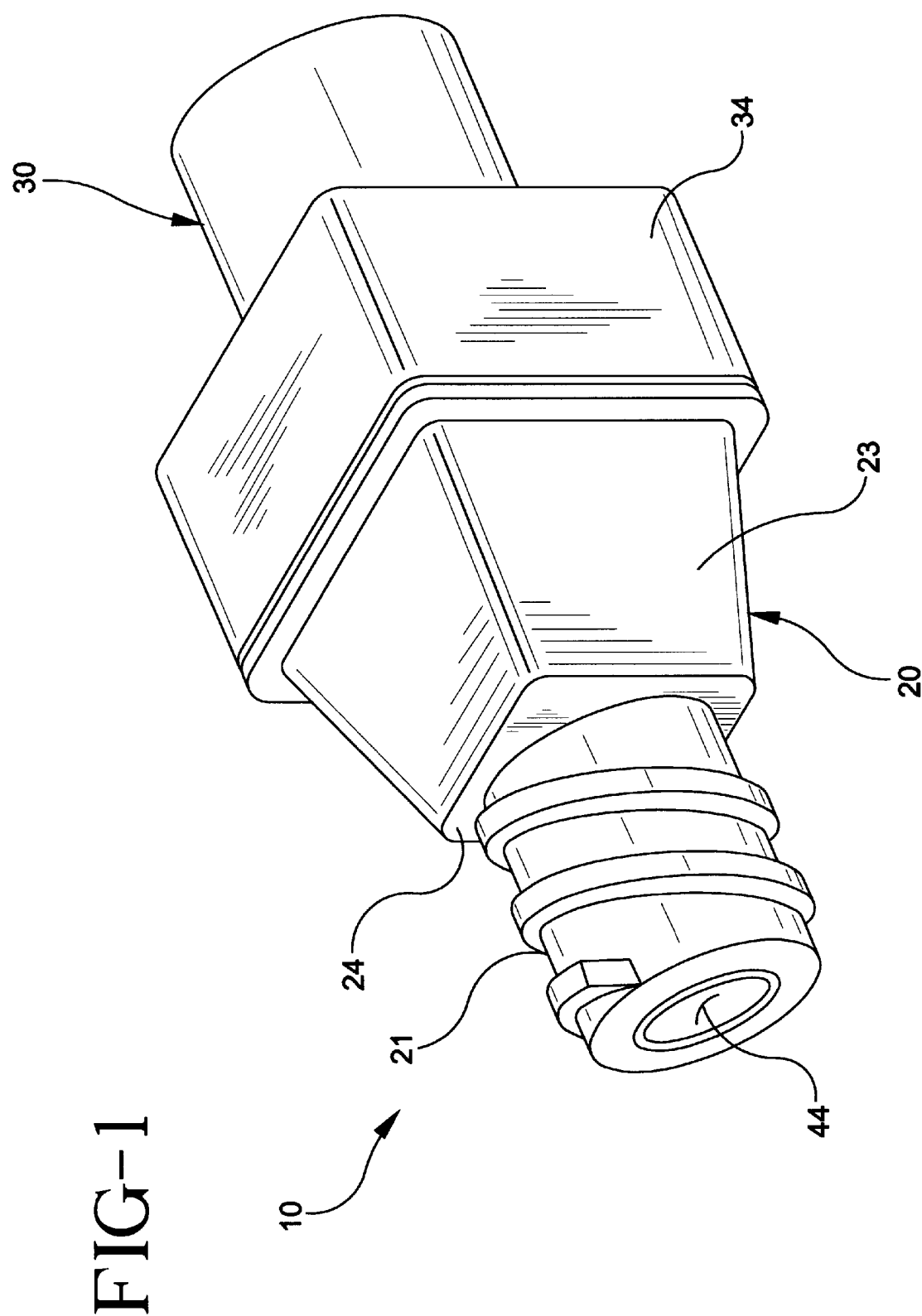
FIG. 1 is a perspective view of a needleless valve connector of the invention.
Figure 2:
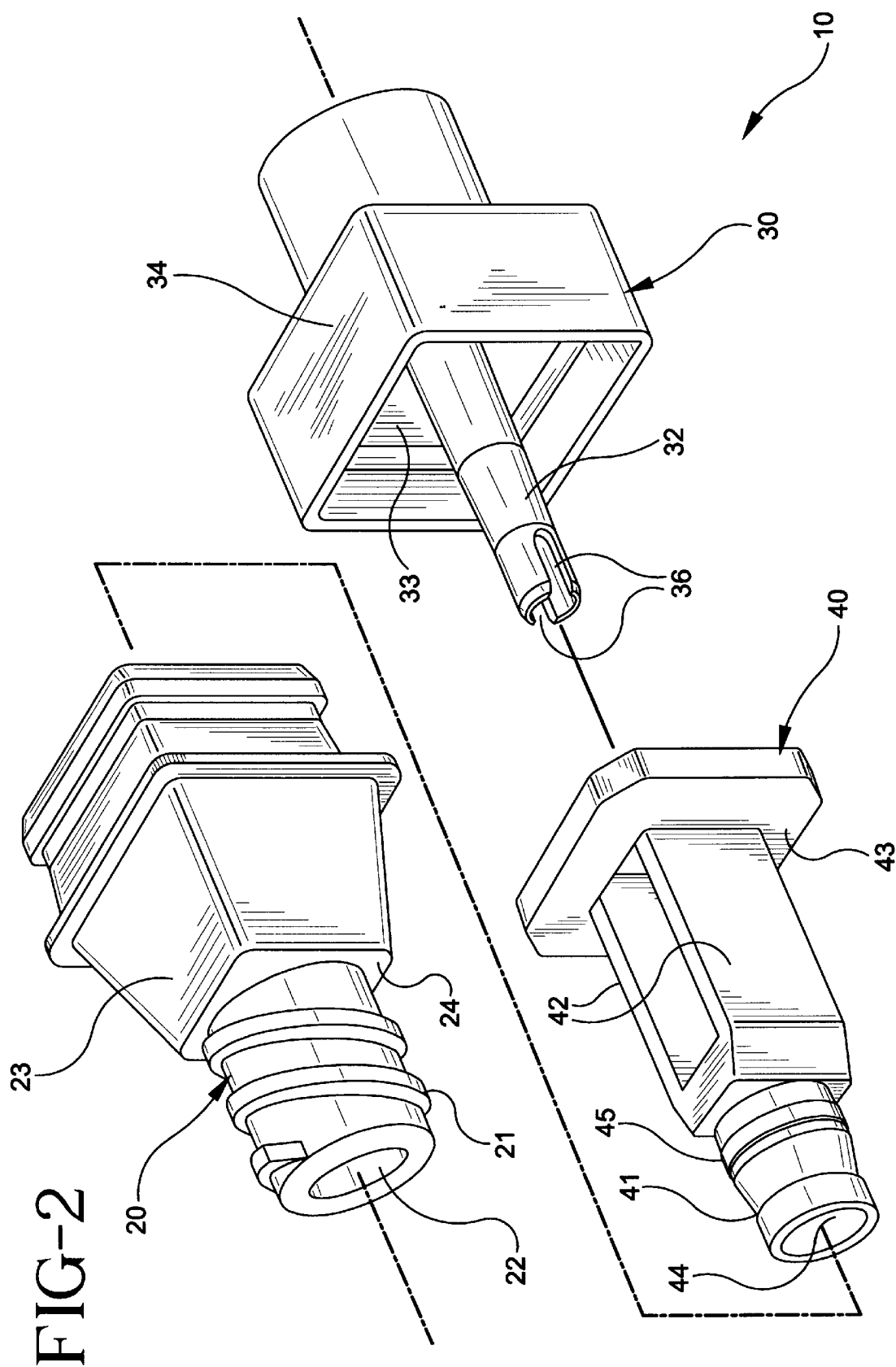
FIG. 2 is an exploded perspective view of a needleless valve connector of the invention.

As used herein, the terms "proximal" and "upper" refer to the portion of the needleless valve connector adjacent to the opening which is accessed by the male luer end of a medical device such as a standard syringe for influx or efflux of fluid and which is at a location closest to the clinician operating the device. Conversely, the terms "distal", "lower" and "down" refer to the portion of the needleless valve connector adjacent to the outlet and which is at a location farthest from the clinician.

The needleless valve connector 10 of the invention comprises three main pieces, an upper body portion 20, a lower body portion 30 and a movable diaphragm assembly 40.

The proximal end of upper body portion 20 defines a neck portion 21 having an inlet opening 22 therein with a female luer configuration. Upper body portion 20 flares outwardly from neck portion 21 to a skirt portion 23 with a shoulder 24 therebetween. Skirt 23 extends from shoulder 24 to the distal end of upper body portion 20 and preferably has a rectangular cross-section.

The distal end of the lower body portion 30 defines an outlet opening 31 having a male luer configuration. Integrally formed and in fluid communication with outlet opening 31 is an internal cannula 32. A base plate 33 extends from the distal end of internal cannula 32 to the outer wall 34 of lower body portion 30. Outer wall 34 engages skirt 23 to define the cavity 50 of needleless valve connector 10. It is to be understood that, although it is preferable that internal cannula 32 be integrally formed with lower body portion 30, both pieces can be separately formed and bonded together by any standard mechanism.

Figure 12:
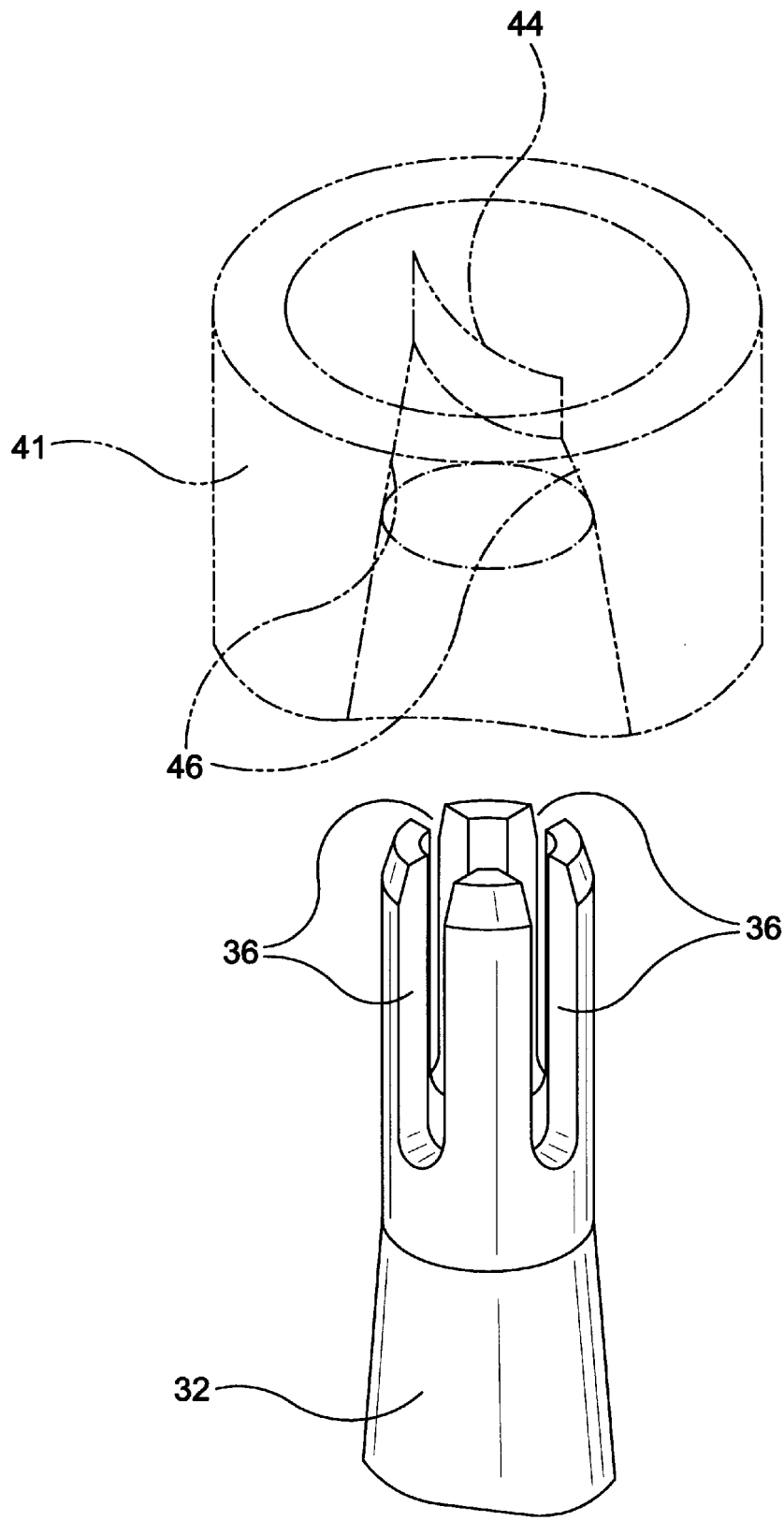
FIG. 12 is a view similar to FIG. 6 but with another configuration for the tip of the internal cannula.
Figure 13:
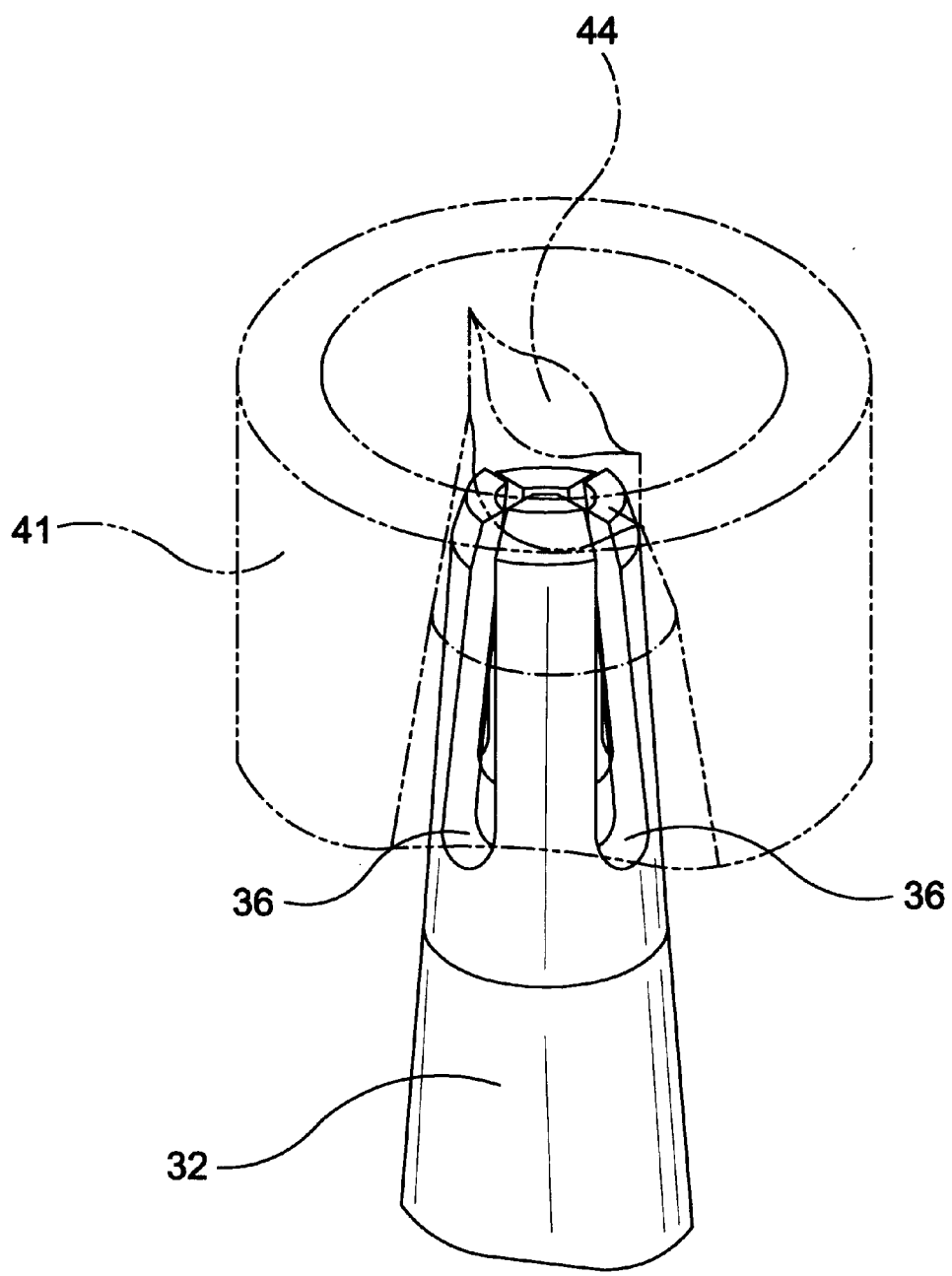
FIG. 13 is a view similar to FIG. 7 but showing the configuration of the tip of the internal cannula of FIG. 12.

Internal cannula 32 defines a lumen 35 extending therethrough. Preferably, the proximal end of internal cannula 32 defines a pair of longitudinally extending diametrically opposed slots 36. These slots 36 should have a width of between about 0.010 inches and about 0.040 inches and a length of between about 0.100 inches to about 0.200 inches. These slots 36 provide the proximal end of internal cannula 32 with some radial flexibility. Specifically, these slots 36 allow the proximal end of internal cannula 32 to be compressed to minimize the diameter of internal cannula 32 at its proximal end. Although the preferred embodiment uses two diametrically opposed slots 36, it is to be understood that any number of slots may be used to provide radial flexibility to the proximal end of internal cannula 32. See for example FIGS. 12 and 13 where four slots are used. The only limiting factor is the structural integrity of the proximal end of internal cannula 32. In other words, if too many slots are used, the proximal end of internal cannula 32 may become too fragile to withstand repeated use of needleless valve connector 10.

Figure 9:
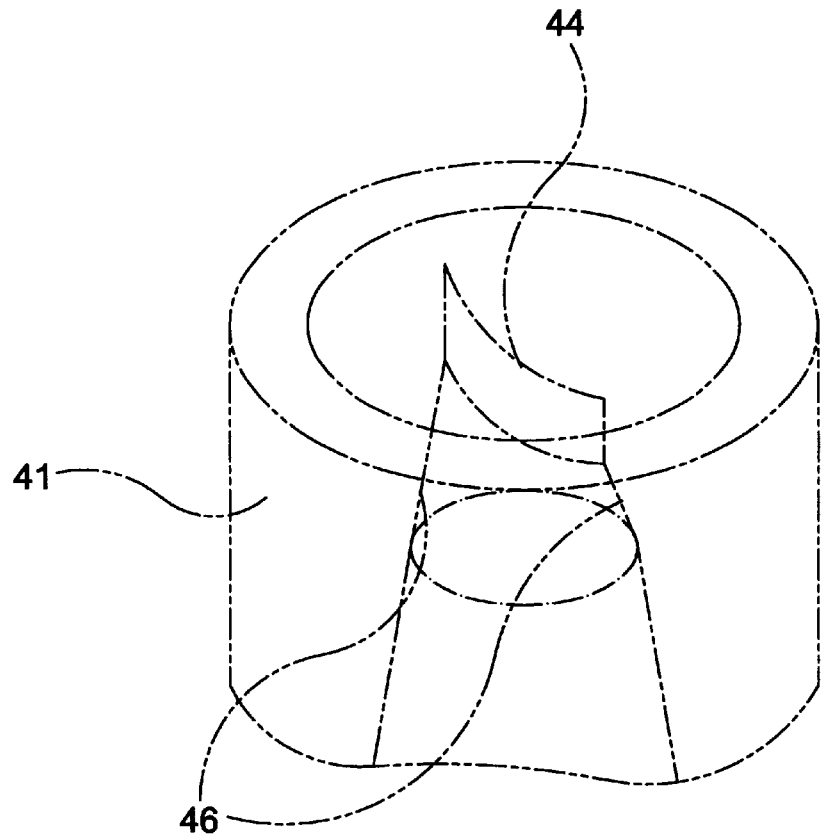
FIG. 9 is a view similar to FIG. 6 but with a different configuration for the tip of the internal cannula.
Figure 9:
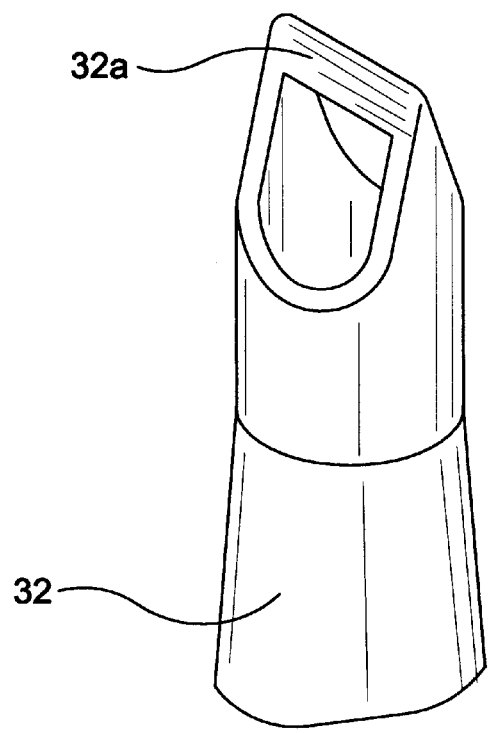
Figure 10:
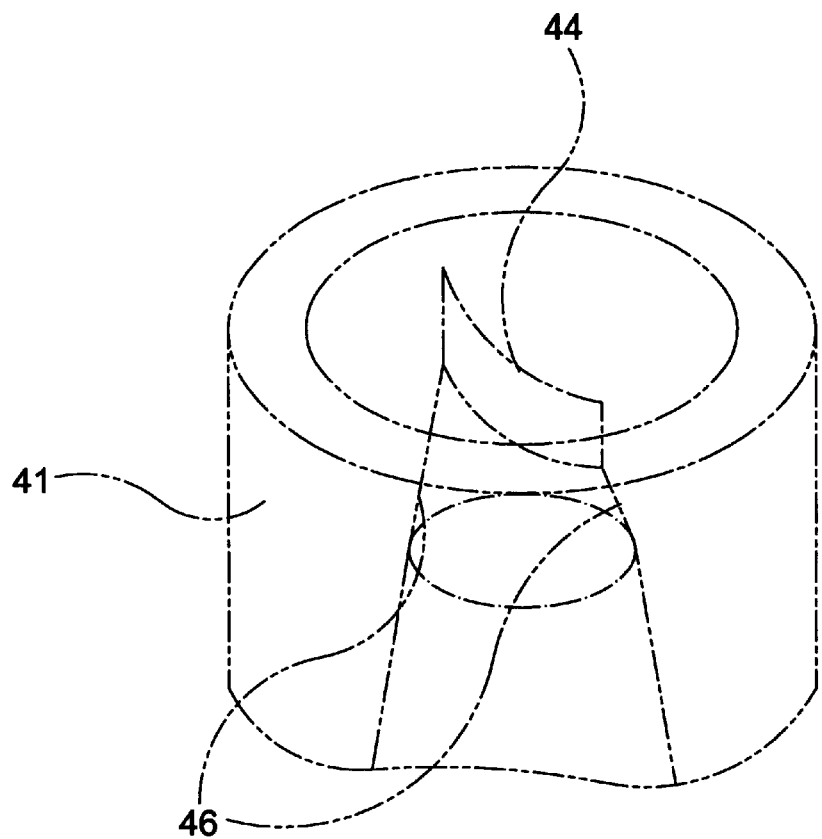
FIG. 10 is a view similar to FIG. 6 but with yet another configuration for the tip of the internal cannula.
Figure 10:
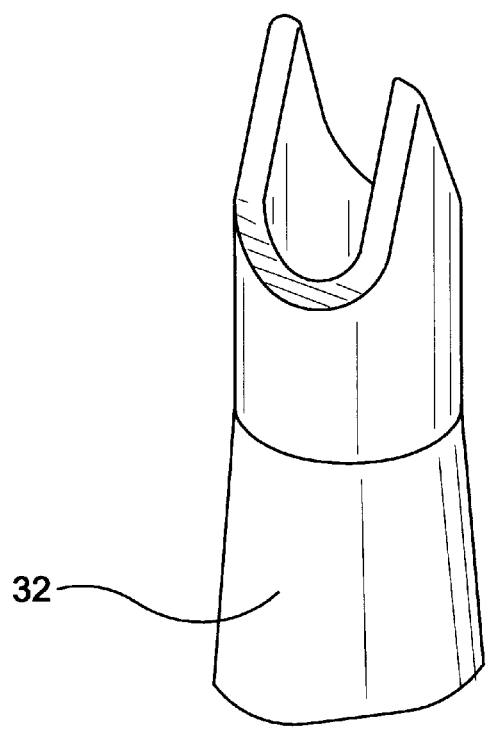
Figure 11:
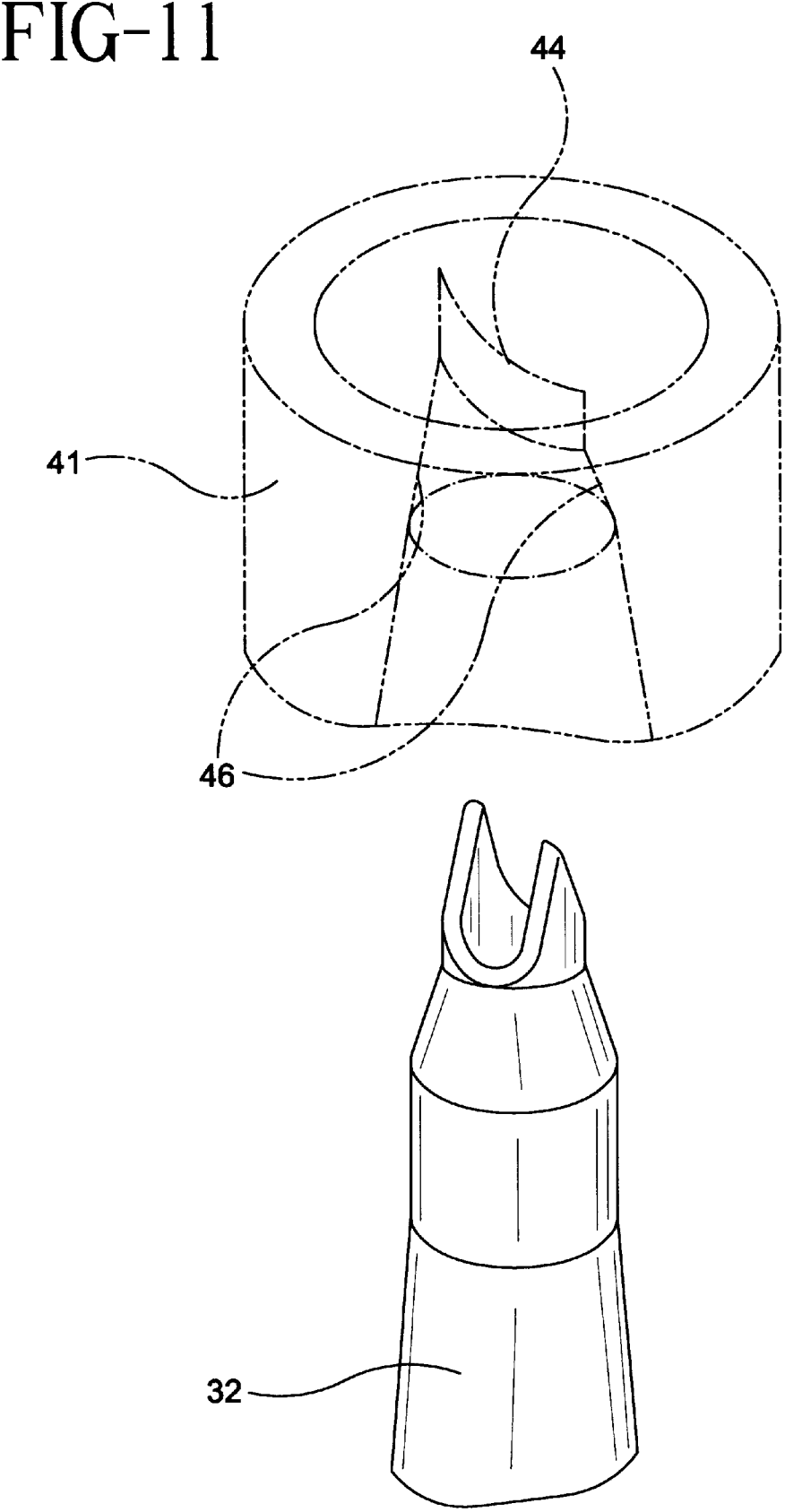
FIG. 11 is a view similar to FIG. 6 but with still another configuration for the tip of the internal cannula.

Alternatively, the proximal end of the internal cannula 32 can be tapered. See for example FIGS. 9–11. This taper can be formed by grinding the proximal end of internal cannula 32 to the desired shape or by molding it to the desired shape. As seen in FIGS. 10 and 11, the proximal end of internal cannula 32 can be open and define two sharp leading edges or, as seen in FIG. 9, the proximal end of internal cannula 32 can include a cross bar 32a over the proximal opening. In both of these configurations it is important that the leading edge of the internal cannula is aligned substantially parallel with the slit to minimize the chances for coring.

Movable diaphragm assembly 40 preferably includes a diaphragm 41, a plurality of flexible legs 42 integrally formed with diaphragm 41 and an annular flange 43 integrally formed with flexible legs 42 at the distal end thereof. These flexible legs 42 provide the biasing force to urge diaphragm 41 toward inlet opening 22. Although flexible legs 42 are preferably integrally formed with diaphragm 41, a separate biasing mechanism, such as a standard spring, could be used and bonded by any standard mechanism to diaphragm 41. Diaphragm 41 defines a slit 44 therein. Diaphragm 41 is oversized in relation to inlet opening 22 to ensure that slit 44 remains closed when needleless valve connector 10 is closed. Diaphragm 41 can simply have a circular cross-section with a diameter larger than the diameter of inlet opening 22. Alternatively, diaphragm 41 could have an oval or elliptical cross-section with a major axis greater than the diameter of inlet opening 22 and a minor axis equal to or less than the diameter of inlet opening 22. Where inlet opening 22 is in the form of a standard female luer configuration with a diameter of 0.170 inches, the major axis preferably is between about 0.171 inches and about 0.200 inches while the minor axis preferably is between about 0.168 inches and about 0.150 inches. The important consideration here is for the perimeter of diaphragm 41 to be at less equal to, but preferably greater than, the internal perimeter of inlet opening 22.

Where the major axis is perpendicular to the length of slit 44, the compressive forces applied to diaphragm 41 by the interaction of diaphragm 41 and inlet opening 22 will be in a direction perpendicular to the length of slit 44 so as to bias slit 44 closed. As used herein, the term "length of slit 44" refers to the line defining slit 44 when viewing movable diaphragm 41 via a top plan view. In addition, an annular seal 45 is formed on movable diaphragm assembly 40 along the proximal portion thereof. Diaphragm 41 should have a durometer of between about 50 Shore A and about 75 Shore A, and preferably between 60 Shore A and 65 Shore A.

The distal end of diaphragm 41 includes at least one and preferably two cams 46 therein. Each cam 46 defines a leading surface that acts as a ramp includes the length of slit 44 at the distal end of diaphragm 41 and that extends away from slit 44 and toward a the distal end of lower body portion 30. Each cam should form an angle with the longitudinal axis of needleless valve connector 10 of between about 40° and about 90° and preferably about 60°.

Figure 4:
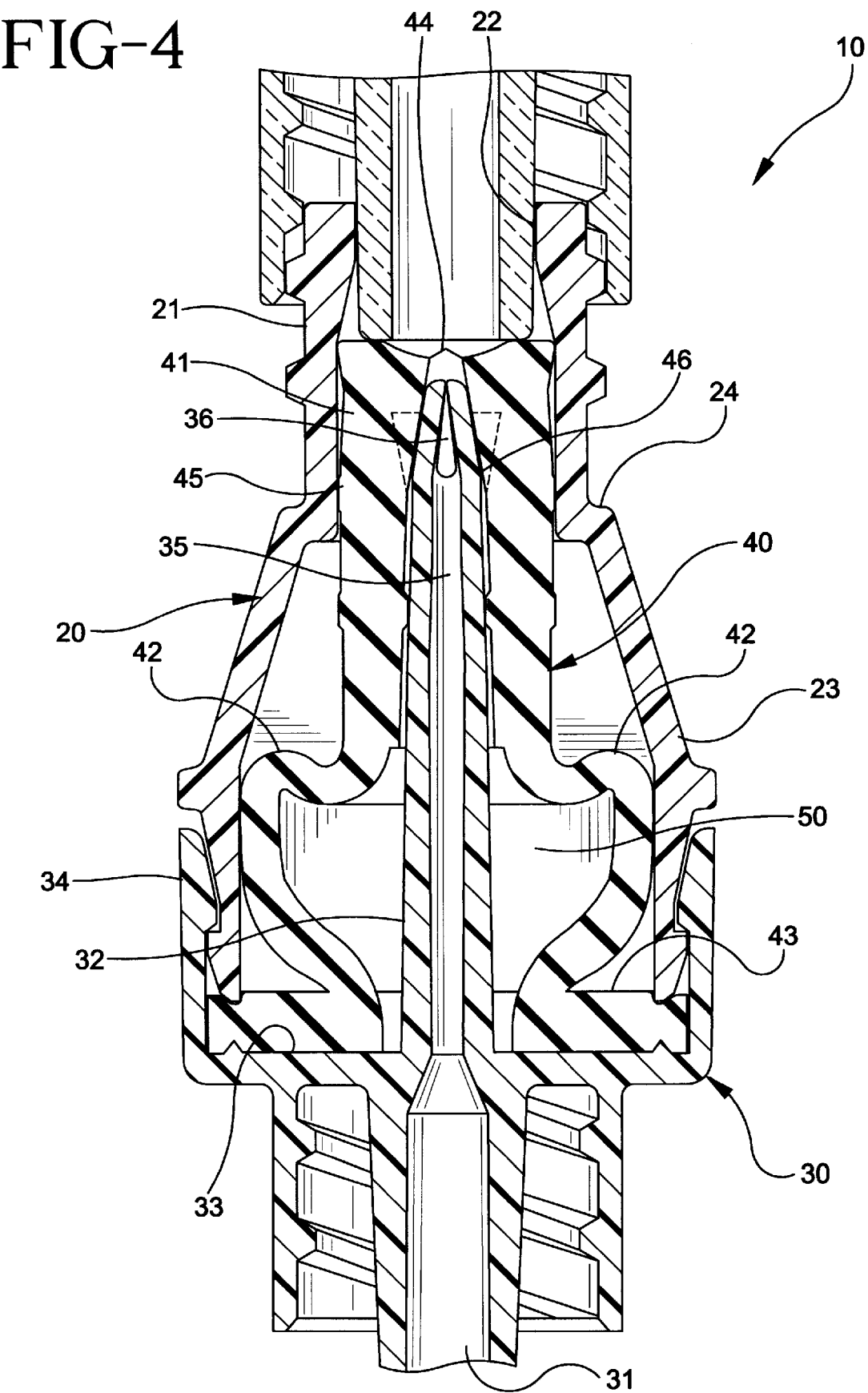
FIG. 4 is a cross-sectional view of a needleless valve connector of the invention with the male luer end of a standard syringe partially inserted therein.
Figure 5:
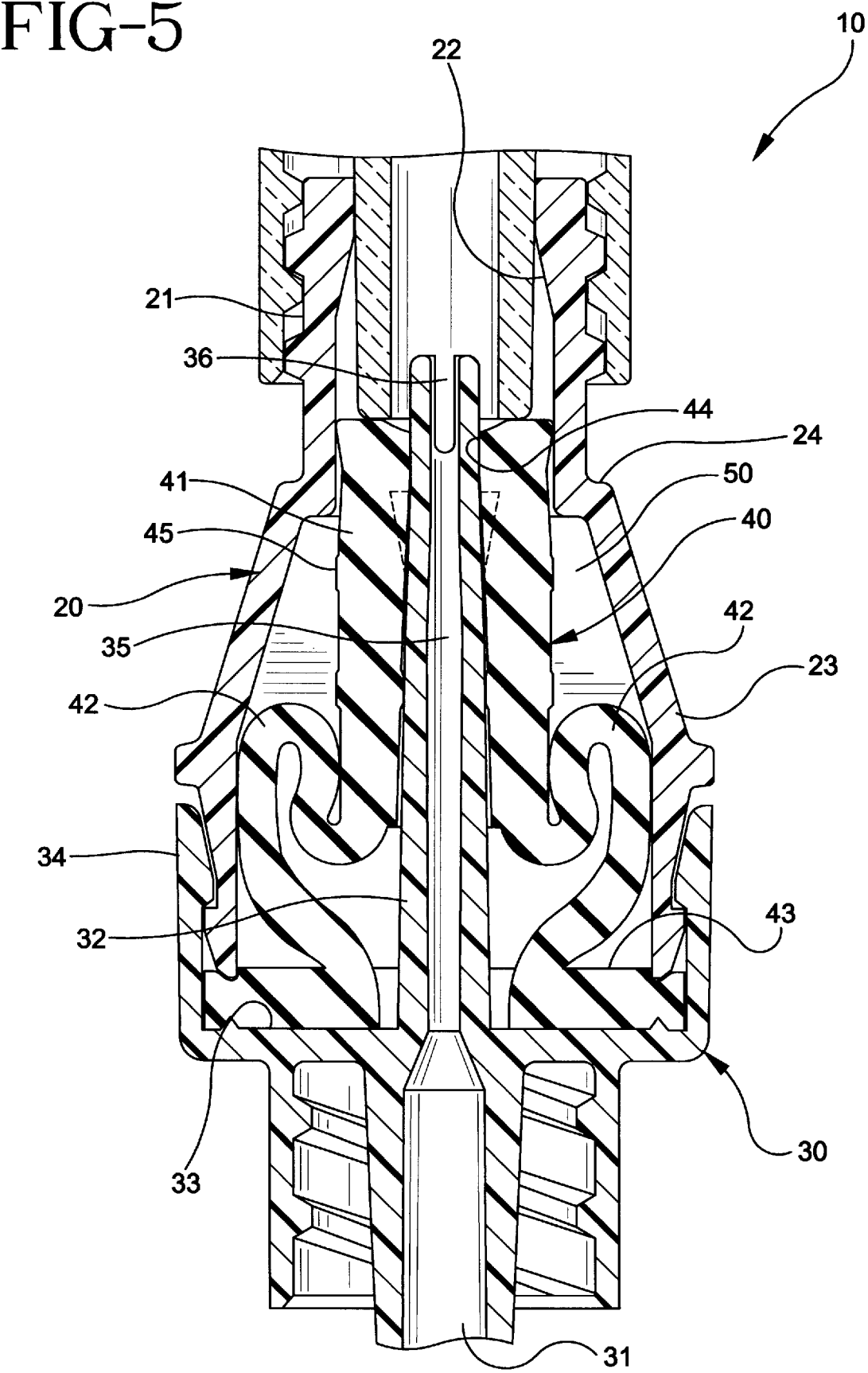
FIG. 5 is a cross-sectional view of a needleless valve connector of the invention in its open position with the male luer end of a standard syringe fully inserted therein and secured thereto.
Figure 6:
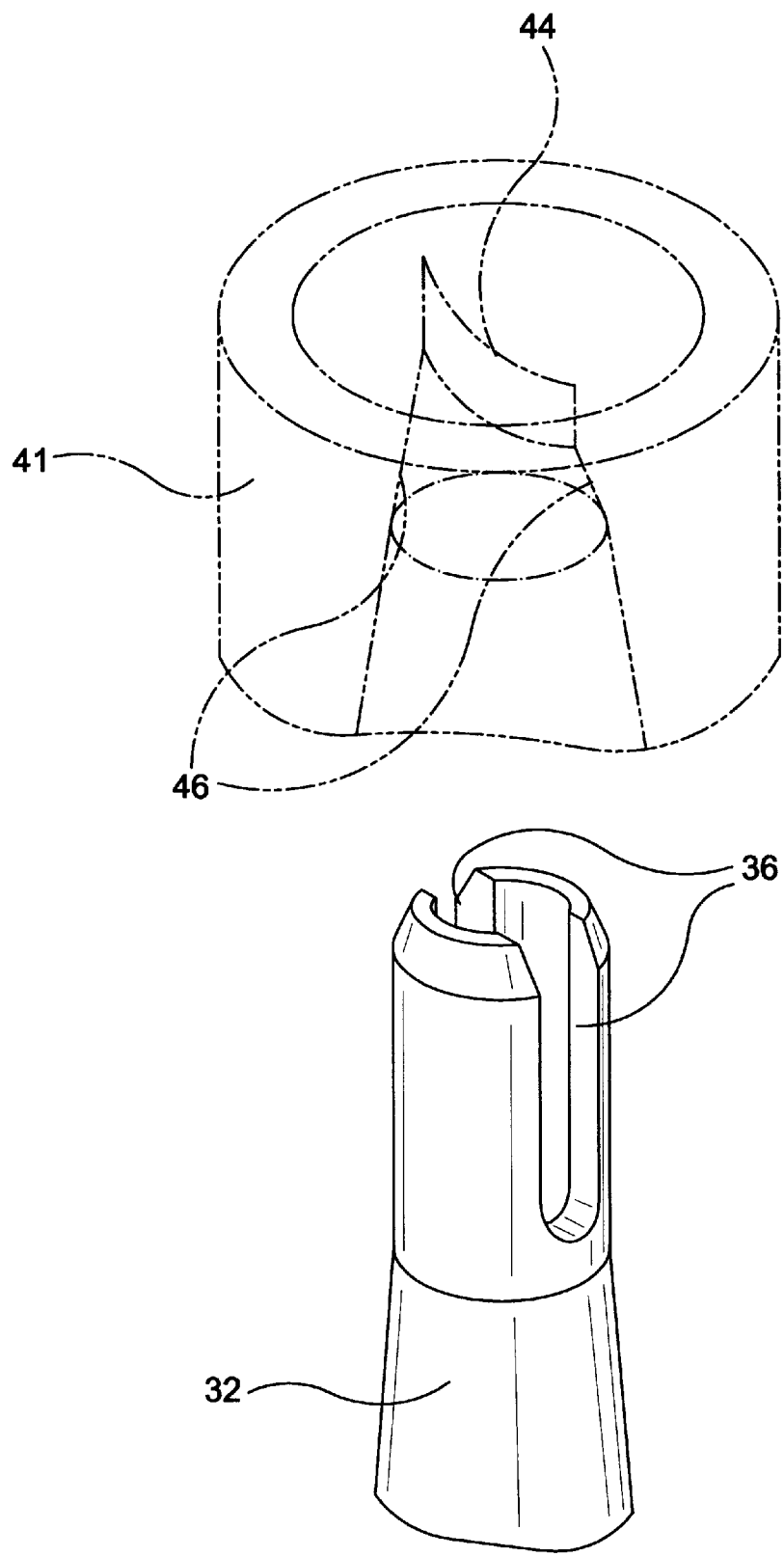
FIG. 6 is an enlarged view of the tip of the internal cannula and a portion of the movable diaphragm of a needleless valve connector of the invention in its closed position.
Figure 7:
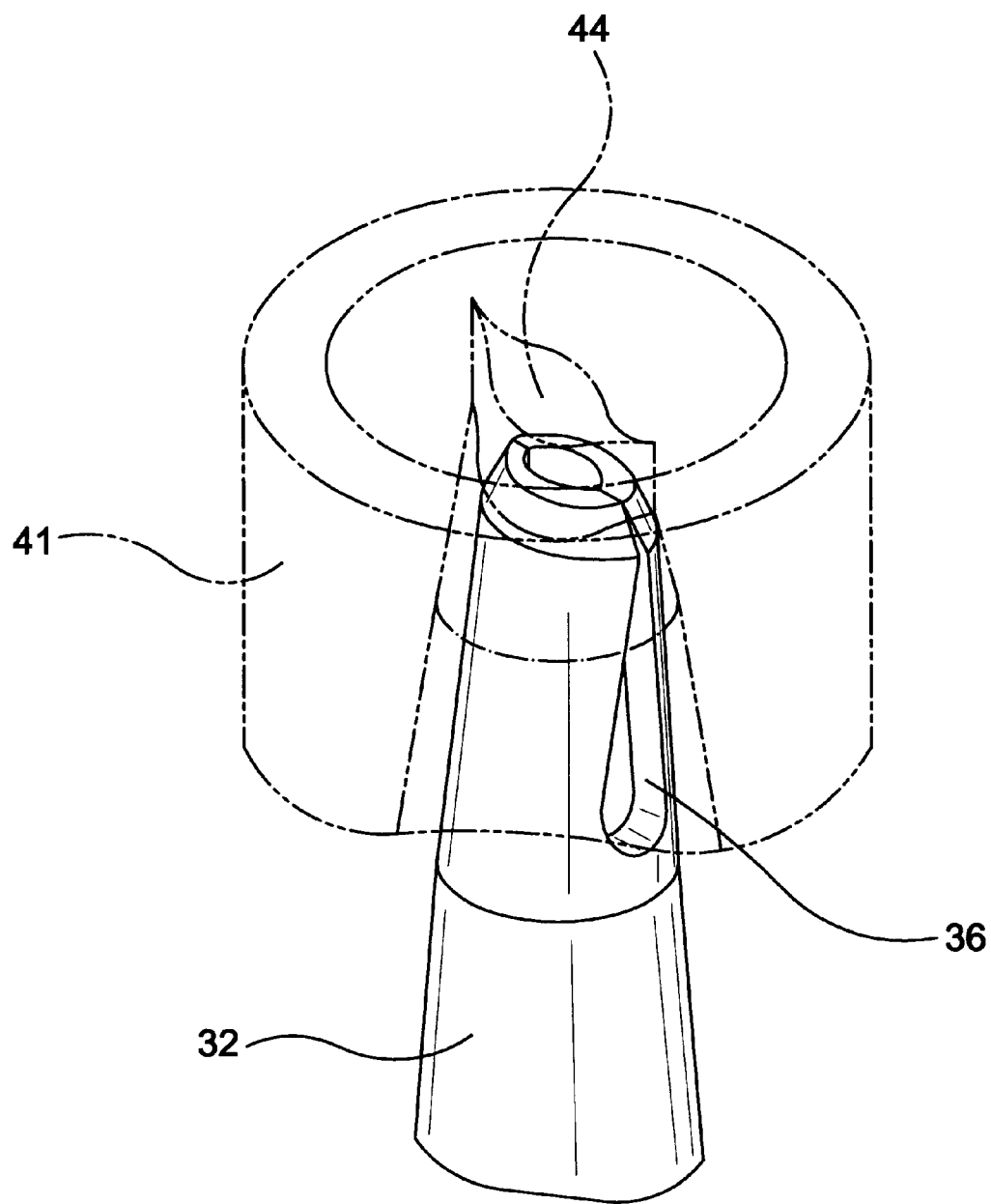
FIG. 7 is a view similar to FIG. 6 but showing the interaction between the proximal tip of the internal cannula and the movable diaphragm when the movable diaphragm is pushed down by the male luer end of a syringe.
Figure 8:
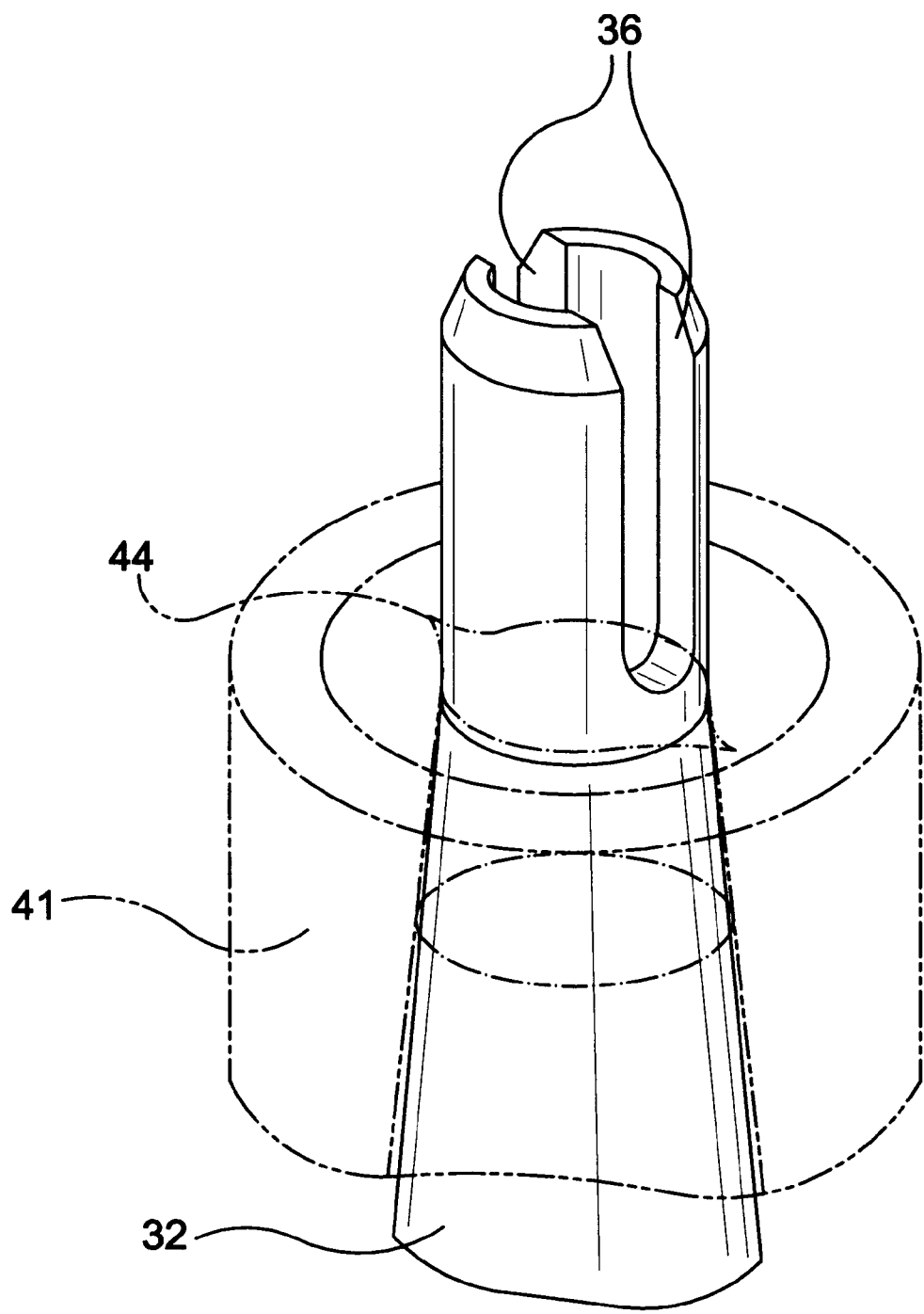
FIG. 8 is a view similar to FIG. 7 when the needleless valve connector of this invention is fully opened.

When two diametrically opposed cams 46 are used and two diametrically opposed slots 36 are used for the proximal portion of internal cannula 32, each slot 36 should be aligned with the length of slit 44 and each cam 46 should be 90° apart from each slot 36. This will ensure that cams 46 can engage the proximal portion of internal cannula 32 between each slot 36. When movable diaphragm assembly 40 is properly aligned with internal cannula 32 and diaphragm 41 is moved distally, e.g. by the male luer end of a syringe, each cam 46 engages a proximal portion of internal cannula 32 between slots 36 during downward movement of diaphragm 41. Further downward movement of diaphragm 41 causes each cam 46 to compress the proximal end of internal cannula 32. See FIGS. 4, 7 and 13. This compression results in the proximal portion of internal cannula 32 having an inclined leading edge, i.e. a tapered surface, and also results in the proximal end of internal cannula 32 having a smaller diameter. This configuration facilitates movement of the proximal portion of internal cannula 32 through slit 44 of diaphragm 41. Once diaphragm 41 has been moved to a position distal of slots 36 of internal cannula 32, the proximal portion of internal cannula 32 is no longer constrained by diaphragm 41. Thus, the proximal portion of internal cannula 32 can return to its original unbiased position and provides an inlet opening to lumen 35 having a diameter substantially equal to the diameter of lumen 35. See FIGS. 5 and 8. Thus, fluid can freely flow through the bore of internal cannula 32.

When the proximal end of internal cannula 32 is tapered, see FIGS. 9, 10, an 11, the angled faces at the proximal end of internal cannula 32 should align with each cam 46 so the leading edge of the proximal end of internal cannula 32 is aligned with the length of slit 44. When this orientation for the engagement between internal cannula 32 and diaphragm 41 is provided, coring is minimized and movement between internal cannula 32 and diaphragm 41 is facilitated.

When the male luer end of a syringe is removed from inlet opening 22, flexible legs 42 act to bias diaphragm 41 proximal of the proximal end of internal cannula 32. Once diaphragm 41 is moved to this position, needleless valve connector 10 is closed preventing fluid flow therethrough.

Although it is preferable to employ both the configuration at the proximal end of internal cannula 32 and cams 46 in this invention, benefits over prior devices can still be enjoyed if only the configuration at the proximal end of internal cannula 32 or only cams 46 are employed. If only the configuration of the proximal end of internal cannula 32 is employed movement through slit 44 is still facilitated and coring is minimized. Where the tapered configuration is used, it is important that the leading edge of the proximal end of internal cannula 32 is aligned with the length of slit 44. Similarly, if only cams 46 are used, cams 46 facilitate opening of slit 44 and minimize coring.

Needleless valve connector 10 is assembled by locating movable diaphragm assembly 40 over internal cannula 32 in lower body portion 30. In this position, flange 43 abuts base plate 33, flexible legs 42 are located about internal cannula 32 and diaphragm 41 is substantially proximal to the proximal end of internal cannula 32 to occlude the inlet opening to internal cannula 32. Upper body portion 20 is placed over internal cannula 32 so that skirt 23 engages outer wall 34 in such a manner that skirt 23, base plate 33 and outer wall 34 act to hold flange 43 against base plate 33. Skirt 23 can be connected to outer wall 34 by any standard means such as frictional or mechanical engagement, chemical adhesive or ultrasonic welding. Because skirt 23 has a rectangular cross-section, skirt 23 acts to properly orient movable diaphragm assembly 40 in upper body portion 20 so that cams 46 can be properly aligned with respect to the proximal end of internal cannula 32. This ensures the proper relationship between the proximal end of internal cannula 32 and diaphragm 41 during distal movement of diaphragm 41.

Figure 3:
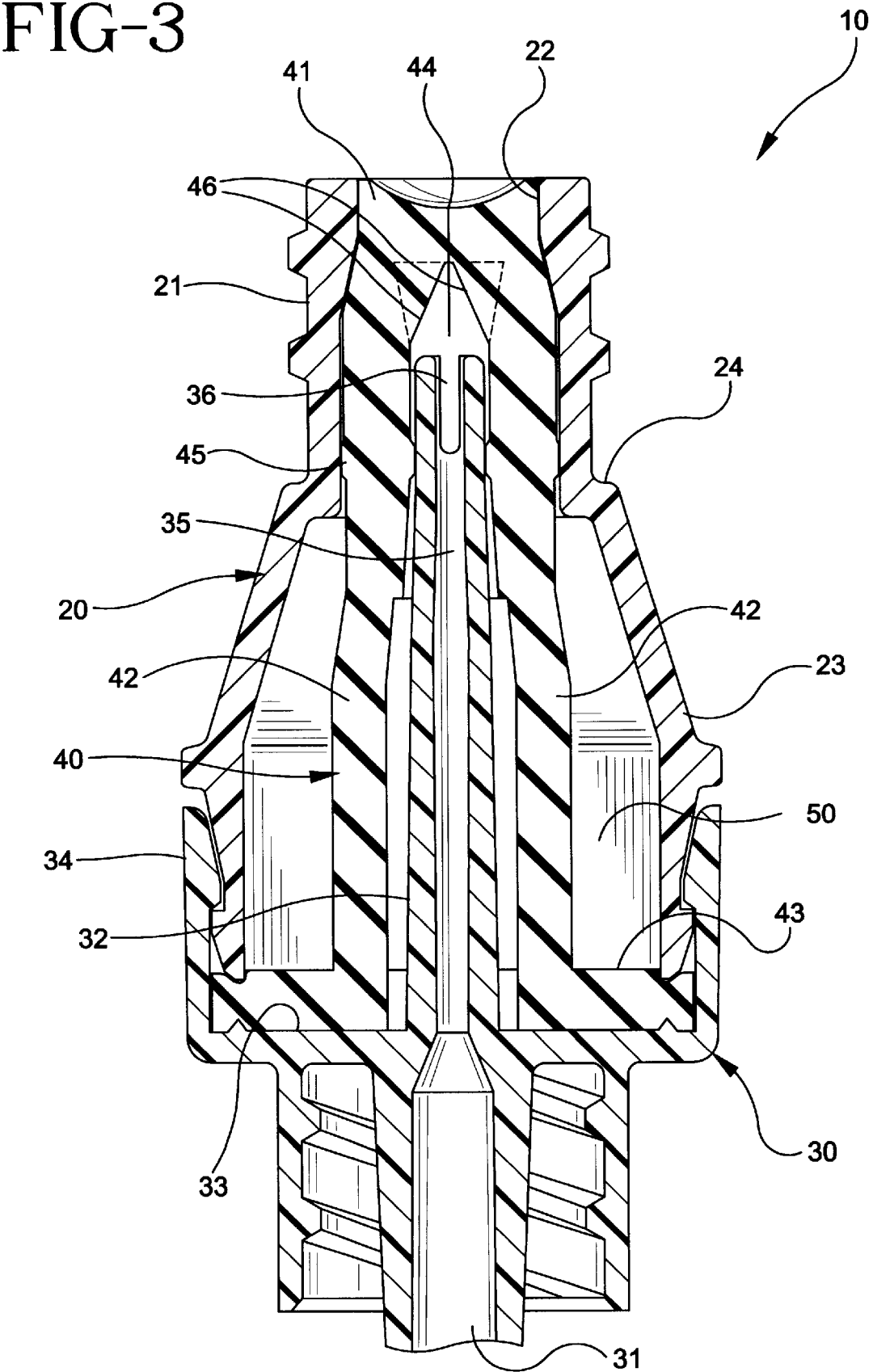
FIG. 3 is a cross-sectional view of a needleless valve connector of the invention in its closed position.

When needleless valve connector 10 is in the position shown in FIG. 3, diaphragm 41 fills inlet opening 22 proximal to the opening to internal cannula 32 so that needleless valve connector 10 is closed to fluid flow. In this position seal 45 abuts neck portion 21 and internal cannula 32 to prevent fluid flow into or out of cavity 50. When needleless valve connector 10 is in the position shown in FIG. 5, diaphragm 41 no longer occludes the inlet opening to internal cannula 32. In this position, needleless valve connector 10 is open to fluid flow.

Thus it is seen that a needleless valve connector is provided that can be accessed without the use of a needle, that eliminates coring of the movable diaphragm by the internal cannula, that eliminates fluid leakage through the movable diaphragm and that is easy to operate.

We claim:

1. A needleless valve connector, comprising:
  a housing defining an interior portion, the housing having a proximal portion defining a proximal opening, a medial portion, and a distal portion defining a distal opening;
  a longitudinally movable diaphragm having a longitudinal axis, a proximal face and a distal face and defining a slit therein extending along the longitudinal axis of the movable diaphragm from the proximal face to the distal face and disposed in the proximal portion of the housing;
  a biasing mechanism adjacent to the movable diaphragm and disposed in the housing to bias the movable diaphragm toward the proximal opening of the housing; and
  an internal cannula axially fixed with respect to the housing and defining a lumen therethrough and disposed in the interior portion and defining a longitudinal axis and having a proximal portion located adjacent to the proximal portion of the housing and a distal portion located adjacent to the distal portion of the housing, the proximal portion is fixed to the internal cannula and has a proximal end with an opening therein axially aligned with the lumen and a plurality of slots therein extending from the opening to a position distal of the opening.

2. The needleless valve connector of claim 1 wherein the plurality of slots in the proximal portion of the internal cannula include two slots located diametrically opposed to one another.

3. The needleless valve connector of claim 2 wherein each slot has a length of between about 0.10 inches and about 0.20 inches and a width of between about 0.01 inches and about 0.04 inches.

4. The needleless valve connector of claim 1 wherein the proximal portion of the internal cannula defines a leading edge which is aligned substantially parallel with the slit.

5. A needleless valve connector, comprising:
  a housing defining an interior portion, the housing having a proximal portion defining a proximal opening, a medial portion, and a distal portion defining a distal opening;
  a longitudinally movable diaphragm disposed in the proximal portion of the housing and having a longitudinal axis, a proximal face and a distal face and defining a slit having a length therein extending along the longitudinal axis of the movable diaphragm from the proximal face to the distal face, wherein the movable diaphragm defines at least one cam defined by an inclined plane that includes the length of the slit at the distal face of the diaphragm and extends away from the slit toward the distal opening and wherein the cam defines a distal portion of the distal face of the movable diaphragm;
  a biasing mechanism adjacent to the movable diaphragm and disposed in the housing to bias the movable diaphragm toward the proximal opening of the housing; and
  an internal cannula axially fixed with respect to the housing and defining a lumen therethrough and disposed in the interior portion and defining a longitudinal axis and having a proximal portion located adjacent to the proximal portion of the housing and a distal portion located adjacent to the distal portion of the housing the proximal portion having a proximal end with an opening therein that is axially aligned with the lumen and a plurality of slots therein extending from the opening to a position distal of the opening wherein the proximal portion is fixed to the internal cannula.

6. The needleless valve connector of claim 5 wherein the proximal portion of the internal cannula defines a plurality of slots therein.

7. The needleless valve connector of claim 6 wherein the plurality of slots in the proximal portion of the internal cannula include two slots located diametrically opposed to one another.

8. The needleless valve connector of any of claims 5 or 6 wherein the cam defines an angle with the longitudinal axis of the movable diaphragm of between about 40° and about 90°.

9. The needleless valve connector of claim 8 wherein the angle is about 60°.

* * * * *